United States Patent [19]
Yarbrough et al.

[11] Patent Number: 5,520,673
[45] Date of Patent: May 28, 1996

[54] ABSORBENT ARTICLE INCORPORATING HIGH POROSITY TISSUE WITH SUPERABSORBENT CONTAINMENT CAPABILITIES

[75] Inventors: Sandra M. Yarbrough, Menasha; Mark L. Robinson, Appleton, both of Wis.; Michael P. Flaherty, Massillon, Ohio

[73] Assignee: Kimberly-Clark Corporation, Neenah, Wis.

[21] Appl. No.: 248,268

[22] Filed: May 24, 1994

[51] Int. Cl.$^6$ .............................. A61F 13/15; A61F 13/20
[52] U.S. Cl. ..................... 604/378; 604/358; 604/385.1
[58] Field of Search ................... 428/290, 311.1, 428/311.7, 315.5, 315.9; 604/358, 365–366, 368, 370, 372, 378, 381–383, 385.1

[56] References Cited

U.S. PATENT DOCUMENTS

| | | |
|---|---|---|
| 3,901,236 | 8/1975 | Assarsson . |
| 4,055,180 | 10/1977 | Karami ..................................... 604/370 |
| 4,076,663 | 2/1978 | Masuda et al. . |
| 4,286,082 | 8/1981 | Tsubakimoto et al. . |
| 4,381,783 | 5/1983 | Elias ........................................ 604/370 |
| 4,585,448 | 4/1986 | Enloe . |
| 4,663,220 | 5/1987 | Wisneski et al. . |
| 4,699,823 | 10/1987 | Kellenberger et al. . |
| 5,028,224 | 7/1991 | Pieper et al. . |
| 5,137,600 | 8/1992 | Barnes et al. .......................... 428/311.5 |
| 5,147,347 | 9/1992 | Huang et al. . |
| 5,192,606 | 3/1993 | Proxmire et al. . |
| 5,411,497 | 5/1995 | Tanzer et al. ............................. 604/372 |

FOREIGN PATENT DOCUMENTS

| | | |
|---|---|---|
| 0217032A3 | 4/1987 | European Pat. Off. . |
| 0532002A1 | 3/1993 | European Pat. Off. . |
| 0539703A1 | 5/1993 | European Pat. Off. . |
| 0615736A1 | 9/1994 | European Pat. Off. . |

*Primary Examiner*—David H. Willse
*Assistant Examiner*—P. Zuttarelli
*Attorney, Agent, or Firm*—Paul Yee

[57] ABSTRACT

A distinctive absorbent article includes a backsheet layer, and an absorbent structure superposed on the backsheet layer. The absorbent structure includes particles of high absorbency material, and a liquid permeable topsheet layer is superposed on the absorbent structure to sandwich the absorbent structure between the topsheet layer and the backsheet layer. A fibrous face sheet layer is incorporated in the article for restraining a movement of the high absorbency material from selected regions of the absorbent structure. The face sheet layer has a Frazier Porosity value of at least about 150 cubic feet per minute per square foot of surface area (cfm/ft$^2$), and has not more than about 100 pores (per 31.37 cm$^2$ of surface area) with a pore size greater than about 300 micrometers.

20 Claims, 11 Drawing Sheets

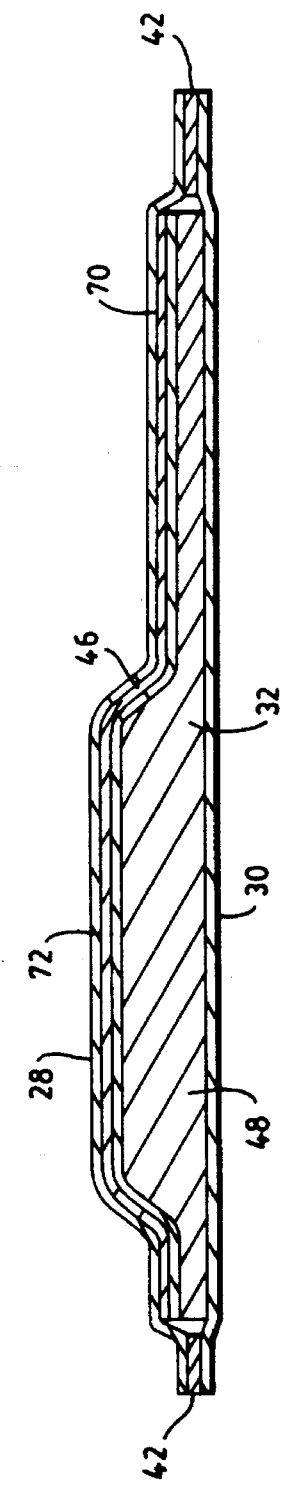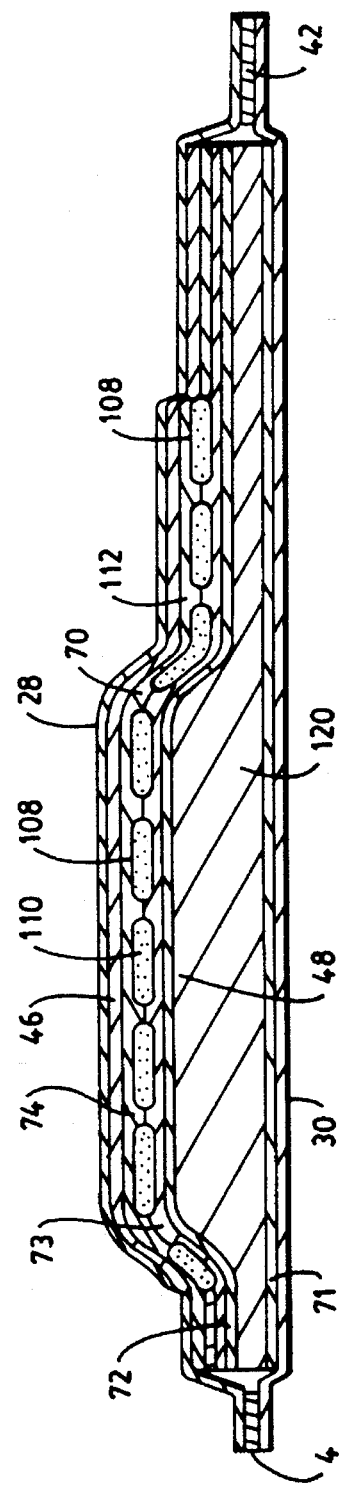

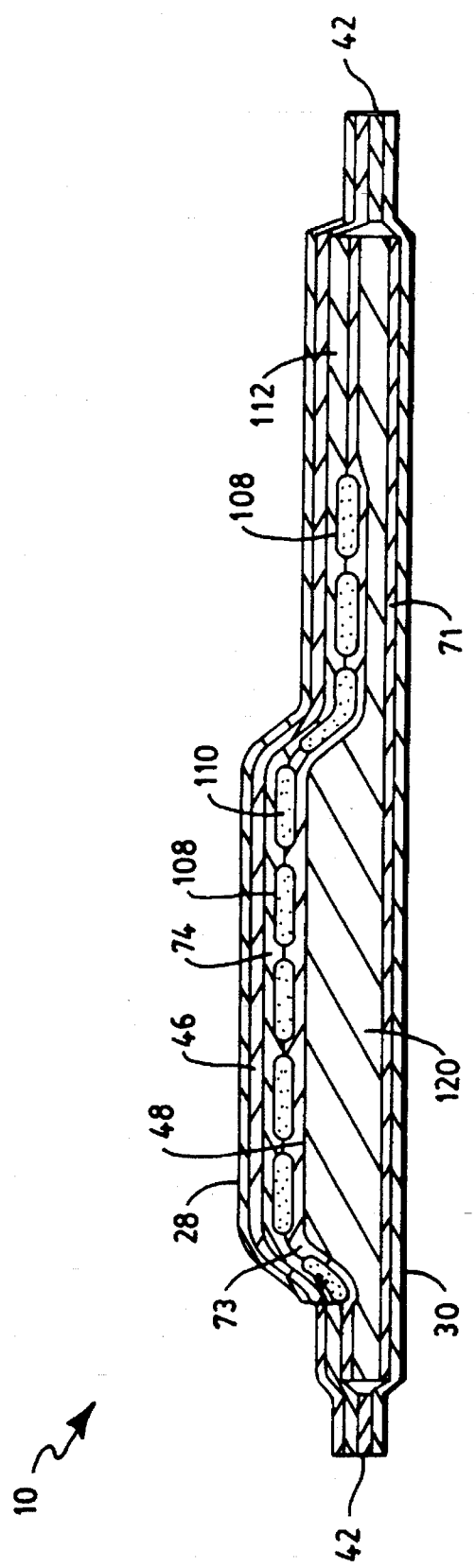

TABLE 1

| CODE | SAMPLE # | AVERAGE POROSITY (cfm/ft^2) | POROSITY RANGE (cfm/ft^2) | 350 RPM SHAKEOUT (mgs) | UNAVAILABLE TEST SHAKEOUT (mgs) | PORE SIZE DISTRIBUTION (# OF PORES) MICROMETER RANGE ||||||| # OF PORES >300 |
|---|---|---|---|---|---|---|---|---|---|---|---|---|
| | | | | | | 50.00-67.97 | 67.97-92.39 | 92.39-125.39 | 125.39-170.73 | 170.73-232.08 | 232.08-315.48 | |
| A | 1-10 | 83 | NA | — | — | — | — | — | — | — | — | — |
| | 11 | — | — | — | — | — | — | — | — | — | — | — |
| | 12 | — | — | — | — | — | — | — | — | — | — | — |
| | 13 | — | — | — | — | — | — | — | — | — | — | — |
| | 14 | — | — | 4 | 16 | — | — | — | — | — | — | — |
| | 15 | — | — | 3 | 4 | — | — | — | — | — | — | — |
| | 16 | — | — | 5 | 11 | — | — | — | — | — | — | — |
| | 17 | — | — | — | — | 1574 | 5610 | 4596 | 2492 | 871 | 209 | 27 |
| B | 1-10 | 261 | NA | — | — | — | — | — | — | — | — | — |
| | 11 | — | — | — | 164 | — | — | — | — | — | — | — |
| | 12 | — | — | — | 411 | — | — | — | — | — | — | — |
| | 13 | — | — | — | 323 | — | — | — | — | — | — | — |
| | 14 | — | — | 100 | 195 | — | — | — | — | — | — | — |
| | 15 | — | — | 294 | 336 | — | — | — | — | — | — | — |
| | 16 | — | — | 286 | — | — | — | — | — | — | — | — |
| | 17 | — | — | — | — | — | — | — | — | — | — | — |
| | 18 | — | — | — | — | — | — | — | — | — | — | — |
| | 19 | — | — | — | — | 612 | 3656 | 6597 | 4602 | 2362 | 882 | 418 |
| C | 1-3 | 311 | NA | — | — | — | — | — | — | — | — | — |
| | 4 | — | — | 240 | — | — | — | — | — | — | — | — |
| | 5 | — | — | 125 | — | — | — | — | — | — | — | — |
| | 6 | — | — | 105 | — | — | — | — | — | — | — | — |
| | 7 | — | — | — | — | 330 | 2177 | 6450 | 4728 | 2643 | 976 | 387 |

FIG. 10

TABLE 1 CONT.

| CODE | SAMPLE # | AVERAGE POROSITY (cfm/ft^2) | POROSITY RANGE (cfm/ft^2) | 350 RPM SHAKEOUT (mgs) | UNAVAILABLE TEST SHAKEOUT (mgs) | PORE SIZE DISTRIBUTION (# OF PORES) MICROMETER RANGE |||||||  # OF PORES >300 |
|---|---|---|---|---|---|---|---|---|---|---|---|---|
| | | | | | | 50.00-67.97 | 67.97-92.39 | 92.39-125.39 | 125.39-170.73 | 170.73-232.08 | 232.08-315.48 | |
| D | 1-10 | 250 | NA | — | — | — | — | — | — | — | — | — |
| | 11-18 | 267 | 256-282 | — | — | — | — | — | — | — | — | — |
| | 19 | — | — | — | 0 | — | — | — | — | — | — | — |
| | 20 | — | — | — | 0 | — | — | — | — | — | — | — |
| | 21 | — | — | 4 | 1 | — | — | — | — | — | — | — |
| | 22 | — | — | — | 0 | — | — | — | — | — | — | — |
| | 23 | — | — | 1 | — | — | — | — | — | — | — | — |
| | 24 | — | — | 2 | 1 | — | — | — | — | — | — | — |
| | 25 | — | — | — | — | — | — | — | — | — | — | — |
| | 26 | — | — | — | — | — | — | — | — | — | — | — |
| | 27 | — | — | — | — | 2870 | 13489 | 9010 | 3588 | 750 | 78 | 14 |
| E | 1-10 | 172 | NA | — | — | — | — | — | — | — | — | — |
| | 11-17 | 178 | 167-186 | — | — | — | — | — | — | — | — | — |
| | 18 | — | — | — | 0 | — | — | — | — | — | — | — |
| | 19 | — | — | 2 | 0 | — | — | — | — | — | — | — |
| | 20 | — | — | 2 | 0 | — | — | — | — | — | — | — |
| | 21 | — | — | 1 | 0 | — | — | — | — | — | — | — |
| | 22 | — | — | — | 0 | — | — | — | — | — | — | — |
| | 23 | — | — | — | — | — | — | — | — | — | — | — |
| | 24 | — | — | — | — | — | — | — | — | — | — | — |
| | 25 | — | — | — | — | — | — | — | — | — | — | — |
| | 26 | — | — | — | — | 2262 | 10727 | 8974 | 4337 | 1326 | 223 | 33 |

FIG. 10A

TABLE 1 CONT.

| CODE | SAMPLE # | AVERAGE POROSITY (cfm/ft^2) | POROSITY RANGE (cfm/ft^2) | 350 RPM SHAKEOUT (mgs) | UNAVAILABLE TEST SHAKEOUT (mgs) | PORE SIZE DISTRIBUTION (# OF PORES) MICROMETER RANGE 50.00-67.97 | 67.97-92.39 | 92.39-125.39 | 125.39-170.73 | 170.73-232.08 | 232.08-315.48 | # OF PORES >300 |
|---|---|---|---|---|---|---|---|---|---|---|---|---|
| F | 1-10 | 208 | NA | — | — | — | — | — | — | — | — | — |
|  | 11-18 | 230 | 209-247 | — | — | — | — | — | — | — | — | — |
|  | 19 | — | — | 38 | — | — | — | — | — | — | — | — |
|  | 20 | — | — | 10 | — | — | — | — | — | — | — | — |
|  | 21 | — | — | 36 | — | — | — | — | — | — | — | — |
|  | 22 | — | — | — | — | — | — | — | — | — | — | — |
|  | 23 | — | — | — | 0 | — | — | — | — | — | — | — |
|  | 24 | — | — | — | 0 | — | — | — | — | — | — | — |
|  | 25 | — | — | — | 0 | — | — | — | — | — | — | — |
|  | 26 | — | — | — | 0 | — | — | — | — | — | — | — |
|  | 27 | — | — | — | 3 | 2654 | 11763 | 9768 | 4981 | 1637 | 310 | 55 |
| G | 1-10 | 241 | NA | — | — | — | — | — | — | — | — | — |
|  | 11-18 | 249 | 228-262 | — | — | — | — | — | — | — | — | — |
|  | 19 | — | — | 4 | — | — | — | — | — | — | — | — |
|  | 20 | — | — | 3 | — | — | — | — | — | — | — | — |
|  | 21 | — | — | 5 | — | — | — | — | — | — | — | — |
|  | 22 | — | — | — | — | — | — | — | — | — | — | — |
|  | 23 | — | — | — | 2 | — | — | — | — | — | — | — |
|  | 24 | — | — | — | 9 | — | — | — | — | — | — | — |
|  | 25 | — | — | — | 0 | — | — | — | — | — | — | — |
|  | 26 | — | — | — | 10 | — | — | — | — | — | — | — |
|  | 27 | — | — | — | 2 | 2749 | 11643 | 9840 | 4869 | 1470 | 261 | 40 |

FIG. 10B

TABLE 1 CONT.

| CODE | SAMPLE # | AVERAGE POROSITY (cfm/ft^2) | POROSITY RANGE (cfm/ft^2) | 350 RPM SHAKEOUT (mgs) | UNAVAILABLE TEST SHAKEOUT (mgs) | PORE SIZE DISTRIBUTION (# OF PORES) MICROMETER RANGE ||||||| # OF PORES >300 |
|---|---|---|---|---|---|---|---|---|---|---|---|---|
| | | | | | | 50.00 - 67.97 | 67.97 - 92.39 | 92.39 - 125.39 | 125.39 - 170.73 | 170.73 - 232.08 | 232.08 - 315.48 | |
| H | 1-10 | 401 | NA | — | — | — | — | — | — | — | — | — |
| | 11-19 | 457 | 398-499 | — | — | — | — | — | — | — | — | — |
| | 20 | — | — | — | — | — | — | — | — | — | — | — |
| | 21 | — | — | 121 | — | — | — | — | — | — | — | — |
| | 22 | — | — | 71 | — | — | — | — | — | — | — | — |
| | 23 | — | — | 83 | — | — | — | — | — | — | — | — |
| | 24 | — | — | — | 22 | — | — | — | — | — | — | — |
| | 25 | — | — | — | 10 | — | — | — | — | — | — | — |
| | 26 | — | — | — | 18 | — | — | — | — | — | — | — |
| | 27 | — | — | — | 14 | — | — | — | — | — | — | — |
| | 28 | — | — | — | 19 | 1186 | 8183 | 11853 | 7743 | 3492 | 984 | 269 |
| I | 1-2 | 248 | 241-255 | — | — | — | — | — | — | — | — | — |
| | 3 | — | — | — | — | — | — | — | — | — | — | — |
| | 4 | — | — | 2 | — | — | — | — | — | — | — | — |
| | 5 | — | — | 1 | — | — | — | — | — | — | — | — |
| | 6 | — | — | 2 | — | 8503 | 10988 | 6367 | 2574 | 499 | 65 | 3 |
| J | 1-2 | 366 | 366 | — | — | — | — | — | — | — | — | — |
| | 3 | — | — | 443 | — | — | — | — | — | — | — | — |
| | 4 | — | — | 253 | — | — | — | — | — | — | — | — |
| | 5 | — | — | 358 | — | — | — | — | — | — | — | — |
| | 6 | — | — | — | — | 3440 | 9052 | 7672 | 4879 | 2253 | 860 | 402 |

FIG. 10C

TABLE 1 CONT.

| CODE | SAMPLE # | AVERAGE POROSITY (cfm/ft^2) | POROSITY RANGE (cfm/ft^2) | 350 RPM SHAKEOUT (mgs) | UNAVAILABLE TEST SHAKEOUT (mgs) | PORE SIZE DISTRIBUTION (# OF PORES) MICROMETER RANGE | | | | | | # OF PORES >300 |
|---|---|---|---|---|---|---|---|---|---|---|---|---|
| | | | | | | 50.00-67.97 | 67.97-92.39 | 92.39-125.39 | 125.39-170.73 | 170.73-232.08 | 232.08-315.48 | |
| K | 1-5 | 263 | 255-272 | -- | -- | -- | -- | -- | -- | -- | -- | -- |
| | 6 | -- | -- | 432 | -- | -- | -- | -- | -- | -- | -- | -- |
| | 7 | -- | -- | 356 | -- | -- | -- | -- | -- | -- | -- | -- |
| | 8 | -- | -- | 417 | -- | -- | -- | -- | -- | -- | -- | -- |
| | 9 | -- | -- | -- | -- | 3857 | 8166 | 6725 | 4352 | 1953 | 626 | 248 |
| L | 1-5 | 193 | 185-201 | -- | -- | -- | -- | -- | -- | -- | -- | -- |
| | 6 | -- | -- | 355 | -- | -- | -- | -- | -- | -- | -- | -- |
| | 7 | -- | -- | 354 | -- | -- | -- | -- | -- | -- | -- | -- |
| | 8 | -- | -- | 235 | -- | -- | -- | -- | -- | -- | -- | -- |
| | 9 | -- | -- | -- | -- | 3935 | 8259 | 6568 | 3592 | 1330 | 354 | 132 |

ABSORBENT ARTICLE INCORPORATING HIGH POROSITY TISSUE WITH SUPERABSORBENT CONTAINMENT CAPABILITIES

TECHNICAL FIELD

This invention relates to absorbent articles, particularly absorbent personal care products. More particularly, the invention relates to absorbent articles which include components which exhibit a high porosity to gas in combination with an improved containment of particulates.

BACKGROUND OF THE INVENTION

Personal care absorbent articles, such as disposable diapers, are typically configured to acquire and retain the body fluids for which the articles were designed, avoid excessive leakage of waste materials from the article and to minimize the amount of any residue which migrates from the absorbent material onto the skin of a wearer. For example, diapers for infants are typically designed to accept large volumes of urine in multiple doses which can measure 60–100 ml per dose. Such diapers often require the use of high absorbency, superabsorbent particles to provide the needed absorbent capacity. Typically, the particles are blended with woodpulp fibers to create an absorbent matrix. The matrix, however, is often unable to adequately contain the superabsorbent particles. As a result, dry particles can escape from the article prior to use, and wet particles can migrate from the absorbent matrix to leave an unsightly gel on the skin of the wearer.

Attempts to alleviate the loss of superabsorbent particles and the migration of superabsorbent gel have employed various types of barrier materials to shield the superabsorbent material from the wearer's skin. For example, nonwoven fabrics composed of meltblown polypropylene fibers have been used as a "wrap" about an absorbent core to contain superabsorbent particles within the core. The generally hydrophobic nature of the polypropylene however, requires that surfactants be employed to minimize the resistance to the penetration of aqueous liquids therethrough. The surfactant must be permanently bound to the nonwoven fabric. Otherwise, the surfactant can be washed away after one or two doses of liquid, and subsequent doses of liquid may undesirably be repelled by the fabric. Although meltblown nonwovens can have excellent integrity and particulate retention properties, the nonwovens can be costly to produce.

To provide desired containment of both wet and dry superabsorbent particles, crepe-wadding or tissue has been employed as a lower cost alternative to meltblown nonwovens. Different types of crepe-wadding, such as forming tissue and barrier tissue, have been employed to produce a combination of properties in absorbent articles. Forming tissue is typically a low basis weight, high porosity wadding employed as a substrate onto which a batt of woodpulp fluff fibers are formed in an airlaying process. Designed to allow the passage of a high volume rate of air flow therethrough, the forming tissue has large numbers of large pores which provide for a low resistance to airflow but are unable to adequately restrain the movement of relatively smaller superabsorbent particles. As a result, such forming tissues have not provided a sufficient barrier to superabsorbent migration. To address this problem, barrier tissues have been configured with small pores to better contain the superabsorbent particles. The barrier tissues have a low porosity which can be obtained by increasing the tissue basis weight and by modifying the fiber content to create increased fiber coverage. Although the barrier tissue was able to reduce the migration of superabsorbent, its low porosity restricted its versatility and necessitated the use of more complicated manufacturing processes.

Thus, conventional absorbent articles, such as those described above, have required more complicated manufacturing processes and more complex constructions to provide adequate performance. Despite the development of absorbent structures of the types surveyed above, there remains a need for absorbent structures which incorporate improved component layers having a high resistance to the migration of particulate superabsorbent material as well as a high permeability to the passage of air.

BRIEF DESCRIPTION OF THE INVENTION

Generally stated, the present invention provides a distinctive absorbent article which includes a backsheet layer, and an absorbent structure superposed on the backsheet layer. The absorbent structure includes particles of high absorbency material, and a liquid permeable topsheet layer is superposed on the absorbent structure to sandwich the absorbent structure between the topsheet layer and the backsheet layer. A fibrous face sheet layer is incorporated in the article for restraining a movement of the high absorbency material from selected regions of the absorbent structure. The face sheet layer has a Frazier Porosity value of at least about 150 cubic feet per minute per square foot of surface area (cfm/ft$^2$), and has not more than about 100 pores (per 31.37 cm$^2$ of surface area) with a pore size greater than about 300 micrometers.

The various aspects of the invention can advantageously provide an absorbent structure which can be less complicated and can be constructed with fewer types of different components while still providing adequate performance. Predetermined component layers in the article can exhibit high permeability and porosity to the passage of air while also providing sufficient resistance to the undesired migration of superabsorbent material. As a result, the face sheet layer can have improved air circulation as well as improved containment of the superabsorbent material. The article can also be manufactured with less complicated processes, and the manufacturing equipment can be more efficiently operated with lower maintenance requirements.

BRIEF DESCRIPTION OF THE DRAWINGS

The invention will be more fully understood and further advantages will become apparent when reference is made to the following detailed description and accompanying drawings in which:

FIG. 4 representatively shows a length-wise, cross-sectional view of an article in which an outerside face sheet layer has been eliminated;

FIG. 5 representatively shows a length-wise cross-sectional view of the article illustrated in FIG. 1, wherein the article has an absorbent structure composed of superabsorbent particles segregated in separate, discrete pockets regions formed in a laminate structure;

FIG. 6 representatively shows a length-wise cross-sectional view of the article illustrated in FIG. 1 wherein the number of face sheet layers has been reduced;

FIG. 10, shows data TABLE 1 for Examples A–C;

FIG. 10A shows a continuation of TABLE 1 for Examples D and E;

FIG. 10B shows a continuation of TABLE 1 for Examples F and G;

FIG. 10C shows a continuation of TABLE 1 for Examples H–J;

FIG. 10D shows a continuation of TABLE 1 for Examples K and L; and

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants, bed pads and the like.

Figure 1:
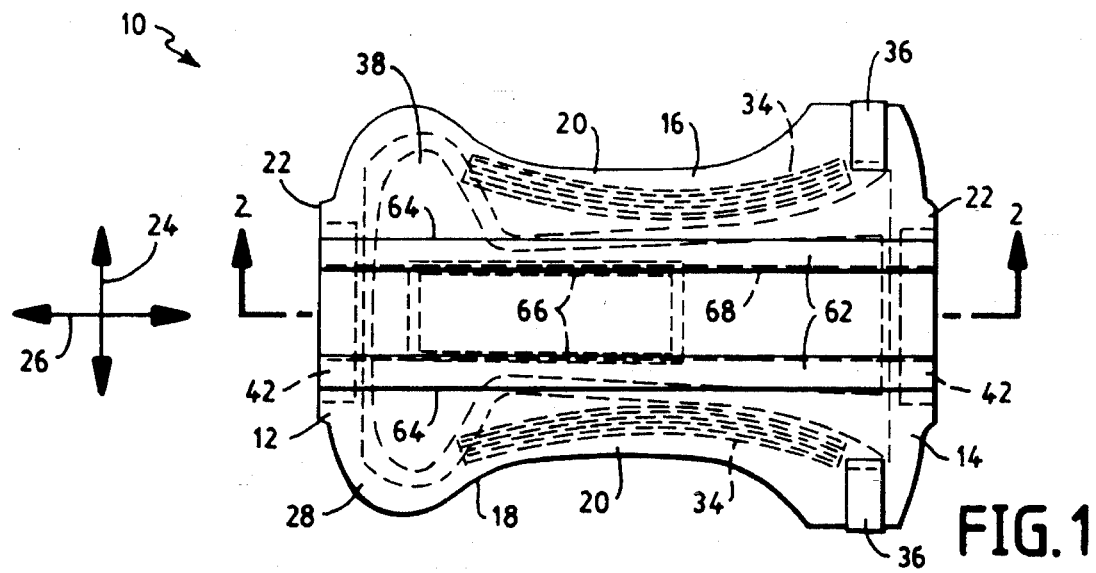
FIG. 1 representatively shows a top plan view of an article of the invention.
Figure 2:
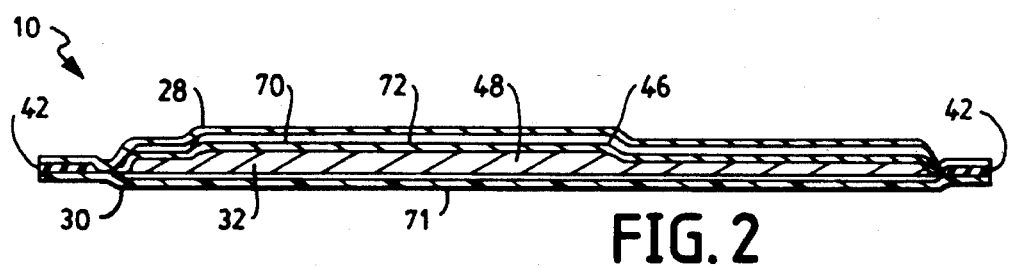
FIG. 2 representatively shows a length-wise, cross-sectional view taken along section 2—2 of the article illustrated in FIG. 1, wherein the article has an absorbent structure composed of superabsorbent particles distributed in a fibrous matrix, and includes a tissue face sheet layer on each of the bodyside and outerside surfaces of the fibrous matrix.

With reference to FIGS. 1 and 2, an absorbent article, such as diaper 10, is representatively shown in its extended, flat-out condition with all elastic contractions and gathers removed. The absorbent article includes a backsheet layer 30, and an absorbent structure 32 superposed on the backsheet layer. A liquid permeable topsheet layer 28 is superposed on the absorbent structure to sandwich the absorbent structure between the topsheet layer and the backsheet layer. A fibrous, liquid-permeable face sheet layer 70 is incorporated in the article for restraining a movement of the high absorbency material from selected regions of the absorbent structure 32. The face sheet layer has a Frazier Porosity value of at least about 150 cubic feet per minute per square foot of surface area (cfm/ft$^2$), and has not more than about 100 pores (per 31.37 cm$^2$ of surface area) which have a pore size greater than about 300 micrometers.

In FIG. 1, the bodyside of the diaper which contacts the wearer is facing the viewer. The shown embodiment of diaper 10 has an intermediate crotch region 16 which interconnects the front and rear waistband regions 12 and 14. The outer edges of the diaper define a periphery 18, along which the longitudinally extending side edge margins are designated 20 and the laterally extending end edge margins are designated 22. Preferably, the side edges are curvilinear and contoured to define leg openings for the diaper. The end edges are shown as straight, but optionally, may be curvilinear. The diaper additionally has a width-wise, transverse dimension 24 and a length-wise, longitudinal dimension 26.

Generally stated, diaper 10 can include a liquid permeable topsheet 28; a substantially liquid impermeable backsheet 30; an absorbent body, such as an absorbent structure 32, positioned and operably connected between the topsheet and backsheet; a surge management layer 46 positioned adjacent a major facing surface of topsheet 28; fastener tabs 36; leg elastic members 34; and waist elastic members 42. The various components of the article may be assembled in a variety of well-known configurations. In addition, the various components of the article may be operably interconnected and attached employing conventional securing mechanisms, such as adhesive bonds, sonic bonds, thermal bonds or any other securing means known in the art. For example, a uniform continuous layer of adhesive, a patterned layer of adhesive, a sprayed pattern of adhesive or an array of separate lines, swirls or spots of construction adhesive may be employed.

In the various aspects of the invention, the absorbent structure can include a retention portion 48 (FIG. 4) having a primary absorbent portion for absorbing and holding absorbed liquids, such as urine. To provide increased levels of absorbent capacity, the retention portion can include particles of high absorbency material having a predetermined range of particle sizes. In particular configurations, such as representatively shown in FIGS. 2 and 4, the retention portion can comprise a blend of fibers and high absorbency material, such as a matrix web of hydrophilic fibers which contains a distribution of superabsorbent particles. A face sheet layer 70 is positioned immediately adjacent at least one major facing surface of the matrix to restrict undesired migration of the superabsorbent material.

In other configurations of the invention, such as representatively shown in FIGS. 5 and 6, the retention portion 48 can comprise a superabsorbent laminate having superabsorbent particles segregated in separate, discrete pockets regions formed in a laminate structure 112. The laminate can include at least one face sheet layer 70 constructed and arranged to provide a carrier layer which holds and maintains the superabsorbent particles in the pocket regions.

The various aspects of the invention can also provide an absorbent article having a surge management portion 46, which may be located on an outerside surface of topsheet 28 which faces toward backsheet 30 (FIG. 2), or alternatively, may be located on an opposite, bodyside surface of the topsheet (not shown). In optional arrangements of the invention, the surge management portion may be cooperatively arranged with a multi-piece topsheet. Such a topsheet configuration can, for example, include two, individual topsheet sections which are laterally spaced-apart from each other along the diaper cross-direction, and an intermediate surge management portion which is operatively connected to bridge therebetween. The surge management portion thereby provides the medial section of the topsheet composite assembly.

Absorbent article structures suitable for use with the present invention are described in U.S. patent application Ser. No. 07/757,778 of D. Proxmire et al., filed Sep. 11, 1991, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), now U.S. Pat. No. 5,192,606 issued Mar. 9, 1993, the disclosure of which is hereby incorporated by reference in a manner that is consistent (not contradictory) with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the disclosure of which is hereby incorporated by reference in a manner that is consistent herewith.

Figure 3:
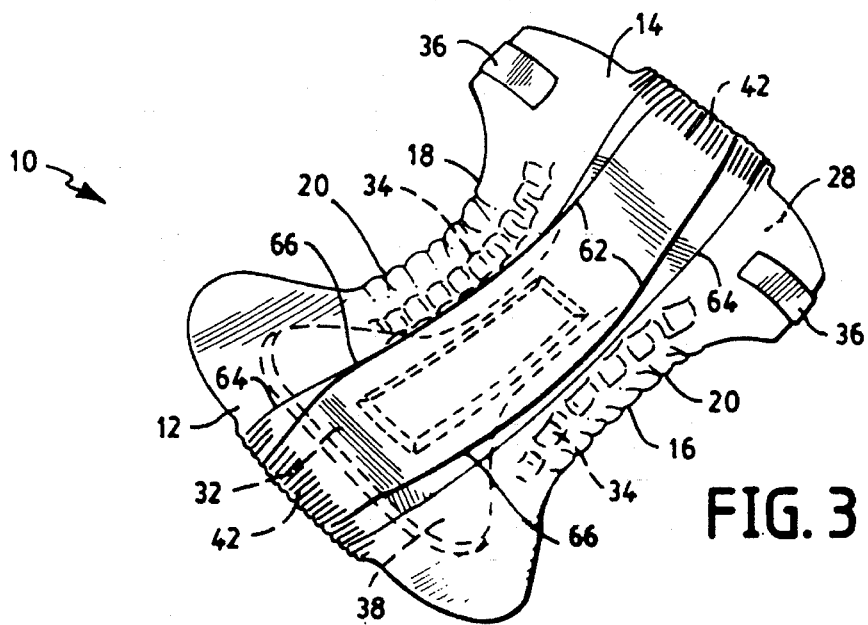
FIG. 3 representatively shows a perspective view of the article in which various elastic members have gathered associated sections of the article.

In the embodiment of diaper 10 representatively shown in FIGS. 1, 2 and 3, topsheet 28 and backsheet 30 can be generally coextensive and can have length and width dimensions which are generally larger than the corresponding dimensions of absorbent structure 32. Topsheet 28 is associated with and superimposed on backsheet 30, thereby defining the periphery 18 of diaper 10, which delimits the outer perimeter or the edges of the diaper 10. The diaper 10 has front and back waistband regions 12 and 14, respectively extending from the laterally extending end edges 22 of diaper periphery 18 toward the transverse center line of the diaper along a distance of from about 2 percent to about 10 percent and preferably about 5 percent of the length of diaper 10. The waistband regions comprise those upper portions of diaper 10, which when worn, wholly or partially cover or encircle the waist or mid-lower torso of the wearer. In particular aspects of the invention, backsheet 30 provides front and/or rear waistbands 12, 14 which are substantially impermeable to liquid. In other aspects of the invention, backsheet 30 can provide front and/or rear waistbands 12, 14 which are substantially impermeable to both liquid and air.

The intermediate, crotch region 16 lies between and interconnects waistband regions 12 and 14. The crotch region comprises that portion of diaper 10 which, when worn, is positioned between the legs of the wearer and covers the lower torso of the wearer. Thus, the crotch region 16 is an area where repeated fluid surges typically occur in diaper 10 or other absorbent article.

Topsheet 28 presents a body-facing surface which is compliant, soft-feeling, and non-irritating when contacting the wearer's skin. Further, topsheet 28 can be less hydrophilic than retention portion 48, and is sufficiently porous to be liquid permeable, permitting liquid to readily penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32.

Various woven and nonwoven fabrics can be used for topsheet 28. For example, the topsheet may be composed of a meltblown or spunbonded web of polyolefin fibers. The topsheet may also be a bonded-carded-web composed of natural and synthetic fibers.

For the purposes of the present description, the term "nonwoven web" refers to a web of material which is formed without the aid of a textile weaving or knitting process. The term "fabrics" refers to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 20 gsm and density of about 0.06 gm/cc. The fabric is surface treated with about 0.28% Triton X-102 surfactant.

In the illustrated embodiment, two containment flaps 62 are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference in a manner that is consistent herewith. Other suitable containment flap configurations are described in U.S. patent application Ser. No. 208,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

Containment flaps 62, in the shown arrangements, are attached to topsheet layer 28 along fixed edges 64 of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. The containment flaps may be constructed of a material which is the same as or different than the material comprising topsheet 28. In optional embodiments, the containment flaps may be constructed of a material which is the same as or different than the material comprising surge management portion 46. The containment flaps may be composed of a material which is air permeable, liquid permeable, substantially liquid impermeable or combinations thereof.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. The backsheet may be a unitary layer of material or may be a composite layer composed of multiple components assembled side-by-side or laminated. The shown embodiment of backsheet 30 includes protruding ear sections which extend laterally at the waistband portions 12 and 14 of the diaper. The ear sections cooperate with the crotch section of backsheet 30 to operably provide leg opening regions for positioning about the legs of the wearer.

In particular embodiments of the invention, backsheet 30 is a polyethylene film having a thickness of from about 0.012 millimeters to about 0.051 millimeters. In the shown embodiment, the backsheet is a film having a thickness of about 0.032 millimeters. Alternative constructions of the backsheet may comprise a woven or nonwoven fibrous web layer which has been totally or partially constructed or treated to impart the desired levels of liquid impermeability to selected regions that are adjacent or proximate the absorbent body.

In a particular aspect of the invention, a terminal edge of the substantially liquid impermeable backsheet material extends to a position which is substantially coterminous with a front or rear waistband edge of the backsheet member. In the illustrated embodiment, for example, a polymer film comprising backsheet 30 extends to a position which is substantially coterminous with a front or rear waistband edge of the backsheet.

Backsheet 30 typically provides the outer cover of the article. Optionally, the article backsheet may comprise one or more separate layers which are in addition to the outer cover layer and may be interposed between the outer cover layer and the absorbent structure. Backsheet 30 may optionally be composed of a micro-porous, "breathable" material which permits water vapor to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size and shape of backsheet 30 is typically determined by the size of absorbent structure 32 and the exact diaper design selected. Diaper 10 may, for example, have a generally T-shape, a generally I-shape or a modified hourglass shape, and can define front and/or rear ear portions 38. The backsheet may extend beyond the terminal edges of absorbent structure 32 by a selected distance. Topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

Fastening means, such as tape tab fasteners 36, are typically applied at the lateral, side ends of the back waistband region 14 of diaper 10 to provide a mechanism for holding the diaper on the wearer in a conventional manner. Tape tab fasteners 36 can be any of those well known in the art, and are typically applied to the corners of diaper 10. Suitable adhesive tape fasteners are described in U.S. Pat. No. 5,147,347 issued Sep. 15, 1992 to Y. Huang et al. (Attorney Docket No. 9871), the disclosure of which is hereby incorporated by reference in a manner that is consistent herewith. Other suitable fastening systems are described in U.S. patent application Ser. No. 168,615 of T. Roessler et al., entitled DYNAMIC FITTING DIAPER and filed Dec. 16, 1993 (Attorney docket No. 10,961), the disclosure of which is hereby incorporated herein by reference in a manner that is consistent herewith.

Elastic members 34 and 42 are disposed adjacent periphery 18 of diaper 10. Along each side edge region 20, leg elastic members 34 are arranged to draw and hold diaper 10 against the legs of the wearer. Waist elastic members may also be disposed adjacent either or both of the end edges 22 of diaper 10 to provide elasticized waistbands.

The various elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design. Elastic members 34 and 42 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several separate, parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive. The various configurations of the invention may have the elastic members located on the inwardmost, bodyside surface of topsheet 28. Alternatively, the elastic members may be interposed between topsheet 28 and backsheet 30.

In the representatively shown embodiments of the invention, the illustrated leg elastic members 34 may comprise a carrier sheet to which are attached a grouped set of elastics composed of a plurality of individual elastic strands. The elastic strands may intersect or be interconnected, or be entirely separated from each other. The shown carrier sheet may, for example, comprise a 0.002 cm thick film of unembossed polypropylene material. The shown elastic strands can, for example, be composed of Lycra® elastomer available from DuPont, a business having offices in Wilmington, Del. Each elastic strand is typically within the range of about 620–1050 decitex (dtx), and can be about 940 dtx in an embodiment of the invention wherein three strands are employed for each elasticized legband.

Leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 1.9–3.8 centimeters (about 0.75–1.5 inches) inward from the outer most edge of the set of elastic strands. In particular arrangements, the curvature of the elastics may not be configured or positioned symmetrically relative to the lateral centerline of the diaper. As representatively shown in FIG. 1, the curved elastics may have an inwardly bowed and outwardly bowed, reflexed-type of curvature, and the lengthwise center of the elastics may be offset by a selected distance within the range of about 0–12 cm toward either the front or rear waistband of the diaper to provide desired fit and appearance.

The shown embodiment of the invention includes a first waist elastic member located at rear waistband portion 14 of diaper 10, and a second waist elastic member positioned at front waistband portion 12. Optional configurations of the invention, however, may include only a single waist elastic member placed at either the front or rear waistband of the diaper. For example, the diaper may include only one waist elastic member located along the rear diaper waistband. Waist elastic 42 can be positioned in the rear end margin 22 provided by backsheet 30, and can be located in a substantially co-linear, cross-directional alignment with the shown pair of fastener tabs 36.

The elastic members can be composed of an elastomeric, cloth-like nonwoven fibrous material, such as an elastomeric stretch-bonded laminate (SBL) web or an elastomeric meltblown web. Examples of suitable meltblown elastomeric fibrous webs for forming the elastic members are described in U.S. Pat. No. 4,663,220 issued May 5, 1987, to T. Wisneski, et al., the disclosure of which is hereby incorporated by reference in a manner that is consistent with the present description. Examples of composite fabrics comprising at least one layer of nonwoven textile fabric secured to a fibrous elastic layer are described in European Patent Application EPA 0 110 010 published Apr. 8, 1987, with the inventors listed as J. Taylor et al., the disclosure of which is hereby incorporated by reference in a manner that is consistent herewith. The composite nonwoven fabrics are commonly referred to as stretch-bonded laminates.

In yet another aspect of the invention, the elastic members can be composed of an elastomeric, stretchable composite web comprising individual, discrete strips of elastomeric material secured to one or more nonwoven fibrous layers. Such a composite web may, for example, comprise an elastomeric meltblown material arranged in a selected pattern of strips and suitably sandwiched and attached between two layers of nonwoven, spunbonded fibrous material. The composite web may alternatively comprise a selected pattern of individual elastomeric strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

An absorbent body, such as absorbent structure 32, is positioned between topsheet 28 and backsheet 30 to form diaper 10. The absorbent body has a construction which is generally compressible, conformable, non-irritating to the wearer's skin. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Alternatively, each piece is connected to an adjacent portion of the absorbent structure by a suitable bonding and/or fiber entanglement mechanism, such as ultrasonic or adhesive bonding, or mechanical or hydraulic needling.

Absorbent structure 32 includes a back section and a front section, and provides a liquid acquisition or target zone. The target zone encompasses the area where repeated liquid surges typically occur in absorbent structure 32. The particular location where liquid is discharged, such as during urination, can vary depending on the age and gender of the wearer. Generally stated, the target zone is a section of absorbent structure 32 which is located in the front 60% of the length of the absorbent structure.

Either or both of the back and front sections can include laterally extending ear regions 38 which provide greater width at the waistband sections of the article. When the diaper is worn, the ear regions are configured to extend about the sides of the wearer's waist and torso. The representatively shown absorbent structure has a contoured, curvilinear periphery, particularly along its side edges. The two generally mirror-image, inwardly bowed, lateral edges provide for a narrower intermediate section suitable for positioning in the crotch of the wearer.

With respect to absorbent articles, wherein reduced bulk or reduced cost may be important, the surge management and retention portions need not extend over the entire, overall shape of the garment. In particular configurations of the invention, for example, retention portion 48 can be asymmetrically located along the length of backsheet 30, with at least about 45 percent of the length of the retention portion located in a front half-section of backsheet 30. Alternatively, at least about 55 percent of the retention portion length is located in the front half-section of backsheet 30, and optionally, at least about 65 percent of the retention portion length is located in the front half-section of the backsheet to provide desired attributes. Similar asymmetric positionings of the surge management portion 46 may also be employed.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In the shown arrangements of the invention, for example, absorbent structure 32 can be generally T-shaped with the laterally extending cross-bar of the "T" generally corresponding to the front waistband portion of the absorbent article for improved performance, especially for male infants. In the illustrated embodiments, the absorbent structure across the ear section of the front waistband region of the article has a cross-directional width of about 9 inches (about 23 cm), the narrowest portion of the crotch section has a width of about 3.5 inches (about 8.9 cm) and the back waistband region has a width of about 4.5 inches (about 11.4 cm).

In a particular aspect of the invention, the absorbent structure has an absorbent capacity of at least about 100 gm of saline. Optionally, the absorbent capacity can be at least about 200 gm of saline. Alternatively, the absorbent structure has an absorbent capacity of at least about 300 gm of saline, and optionally has an absorbent capacity of at least about 400 gm of saline to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

For the purposes of the present invention, the term "hydrophilic" refers to fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for components of the invention can be provided by a Cahn SFA-222 Surface Force Analyzer System. When measured with this system, fibers having contact angles less than 90° are designated "wettable", while fibers having contact angles greater than 90° are designated "nonwettable".

In the various configurations of absorbent structure 32, the retention portion 48, with respect to its total weight, can contain at least about 25 weight percent (wt %) of high absorbency material. Alternatively, the retention portion can contain at least about 50 wt % of high absorbency material, and optionally can contain at least about 75 wt % of high absorbency material to provide desired benefits.

The high-absorbency material employed with the various aspects of the invention may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles.

The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48. Desireable for use are particles having an average size of from about 20 micrometers to about 1 millimeter. A significant proportion of the particles can be less than 300 micrometers in size.

Selected superabsorbent polymers having improved absorbent properties can be important for maximizing the performance while retaining the desired thinness of the absorbent article. For example, in arrangements of the invention having high-absorbency material mixed with hydrophilic fibers, the high-absorbency material can be configured to exhibit a Deformation Under Load which is about 0.6 millimeter or less, alternatively is about 0.4 millimeter or less, and optionally is about 0.3 millimeter or less to provide desired performance. A suitable range is from about 0.3 to about 0.6 millimeter or less. In another aspect of the invention, the high-absorbency material can exhibit a Wicking Index which is about 10 centimeters or greater, alternatively is about 12 centimeters or greater, and optionally is about 18 centimeters or greater to provide desired benefits. A suitable range is from about 12 to about 19 centimeters or greater. The Absorbent Capacity of the high-absorbency material is preferably about 28 grams per gram or greater, preferably is about 32 grams per gram or greater, more preferably is about 36 grams per gram or greater, and still more preferably is about 40 grams per gram or greater. A suitable range is from about 28 to about 41 grams per gram or greater. In other aspects of the invention, the high-absorbency material can exhibit a Wicking Parameter which is about 700 or greater, preferably is about 800 or greater, more preferably is about 850 or greater, and most preferably is about 900 or greater. In further aspects of the invention, the high-absorbency material can exhibit an Absorbency Under Load (measured at a pressure of 0.57 psi) which is about 13 grams per gram or greater, preferably about 17 grams per gram or greater, more preferably is about 20 grams per gram or greater, and most preferably is about 25 grams per gram or greater. A suitable range is from about 13 to about 25 grams per gram or greater. An example of a suitable superabsorbent polymer is SANWET IM3900 polymer, which is available Hoechst Celanese, a business having offices in Portsmouth, Va. Details regarding the determination of the Deformation Under Load, Wicking Index, Absorbent Capacity, Wicking Parameter and Absorbency Under Load are set forth in U.S. patent application Ser. No. 906,001 of S. Byerly et al. filed Jun. 26, 1992 and entitled ABSORBENT COMPOSITES AND ABSORBENT ARTICLES CONTAINING SAME (Attorney docket No. 10174.1), the disclosure of which is hereby incorporated by reference in a manner that is consistent herewith.

In configurations of the invention having the high-absorbency material concentrated within the pocket regions of an absorbent laminate, the high absorbency material can be selected and configured to exhibit an Absorbency Under Load (AUL) value, as determined under a pressure of 0.9 psi (6.2 kPa) of at least about 10 grams of liquid saline per gram of high-absorbency material. Alternatively, the high-absorbency material exhibits an AUL value (at 0.9 psi) of at least about 15 grams per gram, and optionally, exhibits an AUL value (at 0.9 psi) of at least about 20 grams per gram to provide desired performance. The Absorbency Under Load value (at 0.9 psi) of a particular high-absorbency material refers to the amount, in grams, of an aqueous solution of sodium chloride (0.9 weight percent sodium chloride) which 1 gram of superabsorbent material can absorb in 60 minutes while under the selected restraining load.

In configurations of the invention having the high-absorbency material concentrated within the pocket regions of an absorbent laminate, it has been discovered that the performance of a superabsorbent material relates to the ability of the superabsorbent material to absorb a liquid not only while under a single given restraining force, such as about 0.3 pound per square inch (about 2 kPa), but also over a broader range of restraining forces, such as about 0.01–0.9 pound per square inch (about 0.7–6.2 kPa). The ability of a superabsorbent material to absorb a liquid under a variety of different restraining pressures has, for the purposes of this application, been quantified as the Pressure Absorbency Index. The Pressure Absorbency Index is the sum of the Absorbency Under Load values for a superabsorbent material determined under the following loads: 0.01 pound per square inch (0.07 kPa); 0.29 pounds per square inch (2 kPa); 0.57 pounds per square inch (3.9 kPa); and 0.90 pounds per square inch (6.2 kPa). That is, the Absorbency Under Load values for a given superabsorbent material are determined under the restraining forces set forth above according to the method set forth in the document identified below. The Absorbency Under Load values determined under the restraining loads set forth above are then totaled to determine the Pressure Absorbency Index.

Superabsorbent materials useful in the present invention can have a Pressure Absorbency Index of at least about 100, particularly of at least about 105, more particularly of at least about 110, even more particularly of at least about 120; and most particularly of at least about 140.

In configurations of the invention having the high-absorbency material concentrated within the pocket regions of an absorbent laminate, suitable superabsorbent materials may also have a 16-hour extractables level, determined as set forth in the document identified below, of less than about 13 weight percent, particularly of less than about 10 weight percent, more particularly of less than about 7 weight percent, and even more particularly of less than about 3 weight percent.

A particular example of a high absorbency material suitable for use in the absorbent laminate configuration is FAVOR SAB 870 superabsorbent polymer produced by Stockhausen, Inc., a business having offices in Greensboro, N.C.

Suitable techniques for determining the AUL value (0.9 psi), Pressure Absorbency Index and extractables level of the high absorbency material are set forth in copending U.S. patent application Ser. No. 016,312; entitled "ABSORBENT COMPOSITE"; of M. Melius et al.; filed on Feb. 4, 1993 (Attorney Docket No. 10,838); and in its associated continuation-in-part application filed on even date herewith; the disclosures of which are hereby incorporated by reference in a manner that is consistent herewith.

FIGS. 1–4 representatively show examples of a retention portion 48 which comprises a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer melt-blown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the retention portion, with lower concentrations toward the bodyside of the retention portion and relatively higher concentrations toward the outerside of the retention portion. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers. In addition, two or more different types of superabsorbent may be selectively positioned at different locations within or along the fiber matrix.

The invention can, for example, be configured to provide a medium-size article which has been referred to as a "STEP 3" size diaper. Such articles can comprise a retention portion 48 in the form of a fluff pad which includes 4–25 grams of woodpulp fluff. The pad can alternatively include about 5–20 grams of fluff, and can optionally include about 6–15 grams of fluff to provide desired benefits. The woodpulp fluff generally provides shape and form to diaper 10, and carries and positions the particles of superabsorbent polymer or other high-absorbency material. The fluff pad can also contain about 1–16 grams of superabsorbent polymer, and in the shown embodiment, the retention portion can contain 4–12 grams superabsorbent polymer.

The hydrophilic fibers and high-absorbency particles can be configured to form an average composite basis weight which is within the range of about 250–900 gsm. Again, such basis weight is particularly desireable in the target zone of the absorbent structure. In certain aspects of the invention, the average composite basis weight is within the range of about 400–800 gsm, and optionally is within the range of about 450–700 gsm to provide desired performance.

To provide the desired thinness dimension to the absorbent article, retention portion 48 can be configured with a thickness which is not more than about 0.6 cm. Alternatively, the thickness is not more than about 0.53 cm, and optionally is not more than about 0.5 cm to provide improved benefits. For the purposes of the present invention, the thickness is determined under a restraining pressure of 0.2 psi (1.38 kPa).

The density of retention portion 48 or other component of the absorbent article can be calculated from its basis weight and thickness. With respect to diapers, for example, the weight and thickness are measured with respect to samples taken from newly unpacked, unfolded and dry diapers at a restraining pressure of 0.2 psi (1.38 kPa). For measuring thickness, a suitable device is a TMI foam thickness gauge, Model No. TM1-49-21 or its equivalent. The apparatus was obtained from Testing Machines, Inc. of Amityville, N.Y.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material can be distributed down a medial region of retention portion 48 which extends along the length dimension of the retention portion. In addition, the superabsorbent material may have a selected zoned placement to reduce the amount of superabsorbent material located proximate both the side and end edges of the retention portion. The reduced amounts of superabsorbent material at the edges of the retention portion can help improve the containment of the superabsorbent particles within the fibrous fluff matrix of retention portion 48. A pulsed, zoned placement of the superabsorbent material can, for example, be achieved by the method and apparatus described in copending U.S. patent application Ser. No. 07/462,363 of C. Pieper et al. filed Jan. 9, 1990, and entitled "METHOD AND APPARATUS FOR INTERMITTENTLY DEPOSITING PARTICULATE MATERIAL IN A SUBSTRATE" (Attorney Docket No. 8761), the disclosure of which is hereby incorporated by reference in a manner that is consistent herewith.

As representatively shown, the retention portion 48 composed of the absorbent fluff-superabsorbent matrix, can be laminated with or overwrapped in a hydrophilic high wet-strength web provided by one or more face sheets 70. The face sheet can, for example, include a high wet-strength tissue or a synthetic fibrous web. Such an over-lying or overwrapping web can increase the in-use integrity of the absorbent structure. In the configuration shown in FIG. 2, for example, the absorbent structure of the invention can include a bodyside face sheet 72 and an outerside face sheet 71 respectively positioned against the bodyside and outer side surfaces of the absorbent matrix.

The face sheet may comprise a single layer of face sheet material, or may comprise a multi-element sheet which includes a separate bodyside face layer 71 and a separate outerside face layer 72. In the multi-element configuration, each face layer can extend past all or some of the peripheral edges of retention portion 48. Such a configuration of the face sheet layers can, for example, facilitate the formation of a substantially complete sealing and closure around the peripheral edges of retention portion 48. In the back waistband portion of the illustrated diaper, the face sheet material may also be configured to extend an increased distance away from the periphery of the retention portion to add opacity and strength to the back ear sections of the diaper. In the illustrated embodiment, the bodyside and outerside layers of face sheet 70 extend at least about 0.5 inch (about 1.27 cm) beyond the peripheral edges of the retention portion to provide an outwardly protruding, flange-type bonding area over which the periphery of the bodyside face sheet layer may be completely or partially connected to the periphery of the outerside face sheet layer.

The bodyside and outerside layers of a multi-element face sheet 70 may be composed of substantially the same material, or may be composed of different materials. For example, the outerside face sheet 71 may be composed of a relatively lower basis weight material having a relatively high porosity, such as a wet strength cellulosic tissue composed of softwood pulp. Alternatively, either or both of the bodyside and outerside face sheets 71 and 72 can be composed of a material having a small proportion of large pores and having a relatively large proportion of relatively small pores to help reduce the migration of superabsorbent material toward the wearer's skin.

To provide any desired bonding between the individual bodyside and outerside portions of the multi-element face sheet 70, an adhesive can be printed or otherwise applied onto the appointed bonding areas of the face sheet. With reference to the article representatively shown in FIG. 2, for example, a rotogravure-type adhesive applicator may be employed to selectively print a National Starch 33-9156 adhesive composed of a polyvinylacetate-based emulsion. The retention portion 48 can then be placed between the bodyside and outerside portions of face sheet 70, and the mating edges of the face sheet portions can be bonded together to provide a generally complete peripheral seal along substantially the entire perimeter of the retention portion.

The use of the distinctive face sheet material of the invention, however, can advantageously allow a less complex configuration of the invention in which at least one of the face sheets 71 and 72 may be eliminated. As representatively shown in FIG. 4, for example, outerside face sheet 71 can be absent, leaving only the bodyside face sheet 72 to block the migration of superabsorbent material. As a result, the article can be constructed more rapidly at lower cost.

In other aspects of the invention, such as representatively shown in FIGS. 5 and 6, the retention portion 48 can comprise a superabsorbent laminate 112 having particles of superabsorbent material 110 segregated in separate, discrete pockets regions 108 formed in the laminate structure and arranged in a selected array. The laminate 112 can include at least one face sheet layer 70 constructed and arranged to provide a liquid-permeable carrier layer, such as layer 73 and/or 74, which operably holds and maintains the superabsorbent particles in the pocket regions. The absorbent structure can optionally include a supplemental absorbent, such as outerside distribution layer 120. In particular configurations of the invention, the supplemental absorbent can alternatively or additionally include a bodyside distribution layer. Any or all of the distribution layers may also include one or more face sheet layers 70, such as layers 71 and/or 72.

Representative constructions of such absorbent structures are described in U.S. patent application Ser. No. 145,926 entitled "ABSORBENT ARTICLE WHICH INCLUDES SUPERABSORBENT MATERIAL LOCATED IN DISCRETE ELONGATED POCKETS PLACED IN SELECTED PATTERNS" and filed Oct. 29, 1993 by R. Tanzer et al. (Attorney docket no. 10,902), the disclosure of which is incorporated herein by reference in a manner that is consistent herewith.

Within the pocket regions 108 of the superabsorbent laminate 112, the superabsorbent material provides at least about 90 wt % of the total absorbent material located therein. Alternatively, the proportion of superabsorbent material is at least about 95 wt %, and optionally is at least about 98 wt % to provide desired performance. In particular configurations, the article has an superabsorbent laminate 112 which includes about 1–16 gm of superabsorbent material. Alternatively the laminate can include about 4–12 gm of superabsorbent material to provide improved benefits.

With reference to FIG. 5, the illustrated configuration incorporates four face sheet layers composed of porous, liquid permeable, cellulosic tissue material. In particular, distribution layer 120 has a bodyside face sheet 72 positioned generally adjacent a bodyside face surface of the distribution layer and an outer side face sheet 71 positioned generally adjacent an outer side surface of the distribution layer. The absorbent laminate 112 includes two carrier layers, which are provided by bodyside face sheet 74 positioned generally adjacent an bodyside surface of the absorbent laminate and outer side face sheet 73 positioned generally adjacent an outer side surface of the absorbent laminate.

With reference to FIG. 6, the distinctive face sheet material of the present invention can advantageously allow a less complex article construction in which at least one of the face sheet layers may be eliminated. With respect to the absorbent laminate 112, for example, outerside face sheet 73 can be absent, leaving only the bodyside face sheet 74 to block the migration of superabsorbent material from the pocket regions 108. With respect to the distribution layer 120, either or both of the face sheets 71 and 72 may be deleted. As a result, the article can be constructed more rapidly at lower cost.

In particular aspects of the invention, the various face sheets 70 can be configured with a Frazier Porosity value of at least about 150 cfm/ft$^2$. Alternatively, the face sheet porosity is at least about 175 cfm/ft$^2$, and optionally is at least about 200 cfm/ft$^2$ to provide improved benefits.

For the purposes of the present invention, the porosity value of any of the components of the present invention can be determined by ASTM Method D 737-75 "Standard Test Method for Air Permeability of Textile Fabrics", dated Jun. 30, 1975 (reapproved 1980). The method is conducted on a single sheet of the sample material. A permeability testing apparatus of the type suitable for use with this method is a High Pressure Differential Air Permeability Machine, such as available from Frazier Precision Instrument Company located in Gaithersburg, Md.

In other aspects of the invention, face sheet 70 can have not more than about 100 pores (per 31.37 cm$^2$ of surface area) with a pore size greater than about 300 micrometers. Alternatively, the face sheet has not more than about 75 pores, and optionally has not more than about 50 pores (per 31.37 cm$^2$ of surface area) with a pore size greater than about 300 micrometers to provide improved benefits. For the purposes of the present description, the pore size measurement is expressed in terms of equivalent circular diameter (ECD), which is described in detail hereinbelow.

In other aspects of the invention, the face sheet 70 can have at least about 9,500 pores (per 31.37 cm$^2$ of surface area) with a pore size within a range of about 67.97–92.39 micrometers. Alternatively, the face sheet has at least about 10,000 pores, and optionally has at least about 11,000 pores (per 31.37 cm$^2$ of surface area) with a pore size within the range of about 67.97–92.39 micrometers to provide improved performance.

Further aspects of the invention can incorporate a face sheet 70 having not more than about 350 pores (per 31.37 cm$^2$ of surface area) with a pore size within a range of about 232.08–315.48 micrometers. Alternatively, the face sheet can have not more than about 300 pores, and optionally can have not more than about 250 pores (per 31.37 cm$^2$ of surface area) with a pore size within the range of about 232.08–315.48 micrometers to provide desired benefits.

For the purposes of the present invention, the pore size distributions of the face sheet 70 can be determined by employing the Pore Size Measurement procedure set forth in the TESTING PROCEDURES section hereinbelow.

In further aspects of the invention, the face sheet 70 provides for a particle Shake-out value of not more than about 60 mg. Alternatively, the Shake-out value is not more than about 40, and optionally is not more than about 20 to provide improved performance. For the purposes of the present invention, the particle Shake-out value can be determined in accordance with the Shake-Out procedure set forth in the TESTING PROCEDURES section hereinbelow.

With the various aspects of the invention, the basis weight of any of the various face sheets can be at least about 8 grams per square meter (gsm), alternatively can be at least about 12 gsm, and optionally can at least about 16 gsm to desired performance. In a particular aspect of the invention, the basis weight is not more than about 40 gsm, alternatively, is not more than about 35 gsm, and optionally, is not more than about 30 gsm to provide desired advantages. In a further aspect of the invention, the face sheet can have a basis weight which is within the range of about 12–20 gsm, and optionally, is within the range about 14–18 gsm to provide improved effectiveness. In a particular embodiment, the basis weight is about 16 gsm.

Due to the thinness of retention portion 48 and the high superabsorbent concentrations within the retention portion, the liquid uptake rates of the retention portion, by itself, may be too low, or may not be adequately sustained over three insults or doses of liquid into the absorbent structure. The addition of a layer of surge management material into the absorbent structure, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to selected regions of absorbent structure 32, where the liquid can be substantially completely released into retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web composed of natural and synthetic fibers. The surge management portion may be composed of a substantially hydrophobic material, and the hydrophobic material may optionally be treated with a surfactant or otherwise processed to impart a desired level of wettability and hydrophilicity.

The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0–3.0 inch (about 2.54–7.62 cm).

With reference again to FIGS. 2, and 4–6, the absorbent article represented by diaper 10 can include a liquid surge management portion 46 and an absorbent retention portion 48 which is adjacently arranged in a direct, contacting liquid communication with the surge management portion. In the illustrated embodiment, for example, the surge management portion is positioned on the bodyside of retention portion 48. Optionally, the surge management portion may be positioned on the outer side of the retention portion.

In the various embodiments of the invention, at least a part of surge management portion 46 is located within the target zone of the absorbent structure, and in particular arrangements, the surge management portion has an areal extent which extends completely over the target zone. Retention portion 48 is positioned in liquid communication with surge management portion 46 to receive liquids released from the surge management portion and to hold and store the liquid. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The shown arrangement of the surge management portion is substantially free of absorbent gelling material. Surge management portion 46 may, however, contain a very small amount of gelling material to help acquire an initial liquid surge, but the amount should not be excessive. When excessive amounts of absorbent gelling material are maintained in surge management portion 46, however, the gelling material can cause the structure to retain and hold unacceptably high amounts of the liquid. In addition, the transport of liquids away from target zone to other sections of absorbent structure 32, particularly retention portion 48, can be undesirably impaired.

As mentioned previously, surge layer 46 can be a separately formed layer, which lies adjacent the outwardly facing surface of topsheet 28 between the retention portion and topsheet. Thus, surge management portion 46 need not extend through the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in the generally sideways (X–Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized.

In certain embodiments, the surge management portion can be generally rectangular-shaped.

In the various embodiments of the invention, such as the arrangement of FIG. 4 where surge management portion 46 is interposed between topsheet 28 and retention portion 48, the surge management portion can comprise a nonwoven fabric which has a basis weight within the range of about 17–102 gsm and includes at least about 25 wt % of bicomponent fibers to provide a desired bicomponent fiber bond-matrix. Up to 100% of the surge fabric can be composed of bicomponent fibers, and accordingly, 0–75 wt % of the fabric may comprise non-bicomponent fibers. In addition, the fabric can comprise a blend of smaller diameter fibers and relatively larger diameter fibers. The smaller sized fibers have a denier of not more than about 3 d, and alternatively have a denier within the range of about 0.9–3 d to provide desired benefits. The larger sized fibers have a denier of not less than about 3 d, and optionally have a denier within the range of about 3–18 d to provide desired performance. The lengths of the fibers employed in the surge management materials are within the range of about 1–3 in (about 2.54–7.62 cm). The bond-matrix and the blend of fiber deniers can advantageously provide for and substantially maintain a desired pore size structure.

Where surge management portion 46 is alternatively configured for placement adjacent the bodyside of topsheet 28, the surge management portion can be a composite, liner-surge web. The composite web can include a bodyside layer portion and an outside layer portion. The layer portions can be separately laid and can have different structures and compositions. The fibers within each layer and the intermingling fibers between the layer portions are then suitably interconnected (such as by powder bonding, point bonding, adhesive bonding, latex bonding, or by through-air or infrared thermal bonding) to form a composite web. The resultant composite web has a total basis weight of not more than about 102 gsm. Alternatively, the total basis weight is within the range of about 24–68 gsm, and optionally is within the range of about 45–55 gsm. In addition, the total average density of the composite web is not more than about 0.10 g/cc, and optionally is not more than about 0.05 g/cc, as determined at 0.2 psi (1.38 kPa).

Other suitable configurations the surge management portion 46 are described in U.S. Pat. No. 5,192,606 of D. Proxmire et al. issued Mar. 9, 1993 (Attorney docket No. 9932); U.S. patent application Ser. No. 757,760 of W. Hanson et al. filed Sep. 11, 1991 (Attorney docket No. 9922); U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

In the various embodiments of the invention, the surge layer width is within the range of about 16–100% of the topsheet width. The surge layer width is alternatively at least about 24% of the topsheet width, and optionally, is at least 50% of the topsheet width to provide desired levels of effectiveness.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within front section of absorbent structure 32. Thus, surge management portion 46 can be approximately centered about the longitudinal center line of absorbent structure 32, and positioned primarily in central, front section of the absorbent structure 32. In the illustrated embodiment, none of surge management portion 46 is located in the ear regions of the absorbent structure.

With the various embodiments of the invention, the basis weight of surge management portion 46 can be at least about 24 grams per square meter (gsm), alternatively is at least about 40 gsm, and optionally is at least about 45 gsm to help provide the total void volume capacity desired for effective operation. In a particular aspect of the invention, the basis weight is not more than about 300 gsm, alternatively, is not more than about 150 gsm, and optionally, is not more than about 100 gsm to provide desired advantages. It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections.

TESTING PROCEDURES

Pore Size Measurement Procedure:

Testing is conducted on a single sheet of the sample material, and can be conducted with a conventional image analysis system, such as a QUANTIMET 900 Image Analysis System available from Cambridge Instruments (LEICA Corp., Deerfield, Ill.), or a substantially equivalent system. The Quantimet (QMET) 900 system includes an integral Newvicon scanner, which is a high resolution, red-to-infrared sensitive "TV" camera designed especially for image analysis purposes. A Cambridge Macroviewer (obtained from Leica Corp., Deerfield, Ill.) provides a closed lighting cabinet having a 9"×9" opal glass surface which supports the automacrostage described below. The Macroviewer also supports a vertical 48" Polaroid® camera column (Polaroid Corp., Cambridge, Mass.) for mounting the Newvicon scanner over the sample to be measured. Four parallel, linear 75-watt incandescent bulbs are located inside the Macroviewer cabinet to provide a light source during the image analysis. It should be readily apparent to a person of ordinary skill that other comparable tables or stands can be made to provide equivalent capabilities.

The transmitted light produced by the four 75-watt bulbs in the macroviewer is smoothed or made uniform ("flat field illumination") by the opal glass surface on the macroviewer. The intensity of the four bulbs is controlled by two standard variable voltage transformers placed in series, to provide a level of illumination that is within the acceptance range of the scanner.

A 3"×4" black aperture mask is placed directly on top of the opal glass to begin the process of collimating light. The mask restricts the illumination source (bright opal glass) to only that size that would be seen by the optics at the magnification chosen.

A DCI 12"×12" open frame automacrostage, Model HM 121 (obtained from Design Components, Inc., Franklin, Mass.) is employed to provide operator-independent XY linear motion to index the tissue sample from field to field. The autostage is 6" high.

A 12.25"×12.25"×10.25" high black collimating light box is employed to continue the process of collimating light, begun with the black mask described above. Here, the box provides a separation distance between the tissue sample and the masked opal glass.

A 50 mm El-Nikkor enlarging lens (at a suitable aperture setting, such as f/4), and a suitable C-mount adapter coupled to a 40 mm (length) extension tube are employed to form the image of the tissue sheet being measured at a magnification appropriate for the holes observed. The total viewed field width is about 13 mm.

The sample being tested is mounted on 0.25" thick plate glass which is set on top of the collimating box, and a piece of 0.125" thick glass is placed over the sample to hold the sample material flat and to reduce any wrinkles or fold creases.

The field size (STANDARD LIVE FRAME) is equal to 11.63 mm (width), but the actual live frame used here is 8.55 mm in width, to allow large holes to be measured if they fall between this frame and the standard image frame, which is 13.03 mm in width.

The term Equivalent Circular Diameter (ECD) is defined as the diameter of a circle that has the same projected area (A) as the aperture or "bole" being measured in the sample material. The ECD is determined by the equation, $(4A/\pi)^{1/2}$, and is termed "CALC" in the software program listed below.

The term "% A" is defined as 100 times the total area of all holes divided by the actual live frame area, measured on each field-of-view. This is termed TOTPERAR, as listed in the software program that follows.

In the software program, the "Load Shading Corrector" pattern corresponds to a blank field-of-view and can be given any arbitrarily chosen name, such as "BLANKF".

The image analysis can be performed in accordance with the following program, or its equivalent:

```
Cambridge Instruments QUANTIMET 900 QUIPS/MX : V03.02
ROUTINE: WRAP1      RUN: 0      SPECIMEN:
Enter specimen identity
Scanner    ( No. 2 Newvicon    LV = 0.00    SENS = 1.64 )
Load Shading Corrector ( pattern - BLANKF )
Calibrate User Specified ( Calibration Value = 14.54 micrometers
   per pixel )
CALL STANDARD
TOTPERAR: = 0
```

```
TOTFIELDS: = 0
Stage Scan    (         X                  Y
    scan origin    15000.0           25000.0
    field size      4000.0            4000.0
    no of fields       7                 7            )
Detect 2D      ( Lighter than 32 PAUSE )
For FIELD
Scanner      ( No. 2 Newvicon AUTO-SENSITIVITY LV=0.00 )
Live Frame is Rectangle ( X: 135, Y: 145, W: 588, H: 515, )
Image Frame is Standard Image Frame
Detect 2D (Lighter than 32)
Amend     ( CLOSE by 1 )
Amend     ( OPEN by 1 )
Measure field - Parameters into array FIELD
PERCAREA := 100. * FIELD AREAFRACT
TOTPERAR := TOTPERAR + PERCAREA
TOTFIELDS := TOTFIELDS + 1.
Measure feature    AREA    FERET 0    FERET 90
    into array FEATURE (of 700 features and 4 parameters)
FEATURE      CALC :=   ( ( 4. * AREA / PI ) -> 0.50000 )
Distribution of COUNT v CALC from FEATURE in HIST01
    from 50.00 to 5000.00 in 15 bins (LOG)
Distribution of COUNT v CALC from FEATURE in HIST02
    from 0.00 to 5000.00 in 10 bins (USER DEFINED)
Stage Step
Next FIELD
Print " "
Print Distribution (HIST01, differential, bar chart, scale =
    0.00)
Print " "
Print " "
Print Distribution (HIST02, differential, bar chart, scale =
    0.00)
Print " "
Print " "
Print "TOTAL AREA SCANNED (sq cm) = ", CL.FRAREA * FIELDNUM /
    1.0000E+08
Print " "
Print "AVE PERCENT AREA (%A), HOLES = ", TOTPERAR / TOTFIELDS
for LOOPCOUNT = 1 to 12
Print " "
Next
End of Program
```

Shake-Out Test Procedure:

Sample Preparation

Figure 8:
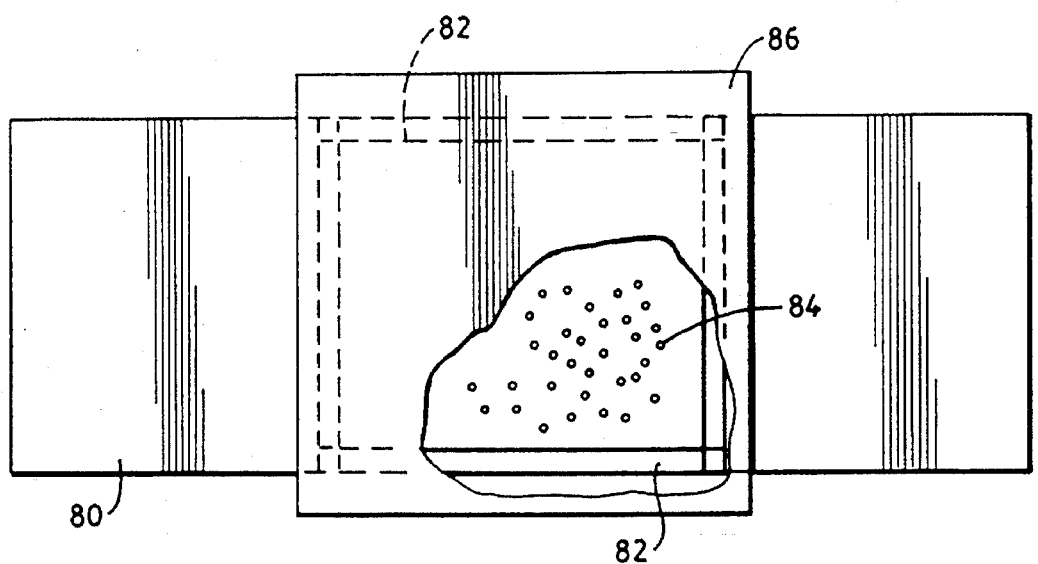
FIG. 8 representatively shows a partially cut-away, top plan view of a representative sample mount and test sample employed for testing.
Figure 9:
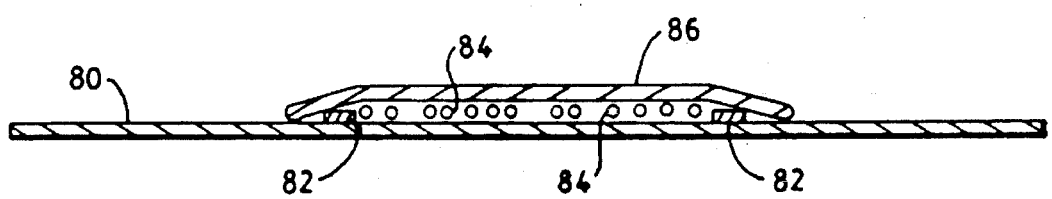
FIG. 9 representatively shows a side view of the sample mount and test sample illustrated in FIG. 8.

With reference to FIGS. 8 and 9, a 4 inch by 11 inch sample mount 80 is cut from a 350 gsm cellulose paper (or an equivalent material which provides suitable structural integrity with enough bending flexibility to allow an insertion of the sample mount 80 into the test unit).

A 0.25 in wide, two-sided pressure sensitive adhesive tape 82, such as 3M Scotch™ brand 2 mil, high tack adhesive transfer tape (#465) or equivalent, is applied to the center of the sample mount to form a square "window frame" having outside dimensions of 4 inch by 4 inch. 500 mg (±5 mg) of superabsorbent material 84 is placed in the center of the "window frame." The particle size distribution of the superabsorbent material is determined by conventional sieve analysis, and was as follows:

212–300 micrometers: 40% (by weight)

149–212 micrometers: 35%

90–149 micrometers: 25%

Testing is conducted on a single sheet of the sample material 86, and a 4.5 inch by 4.5 inch piece of the sample tissue being tested is placed over the framed area and adhered by pressing the tissue onto the adhesive tape to provide a tight seal.

Shake Test Unit

Figure 7:
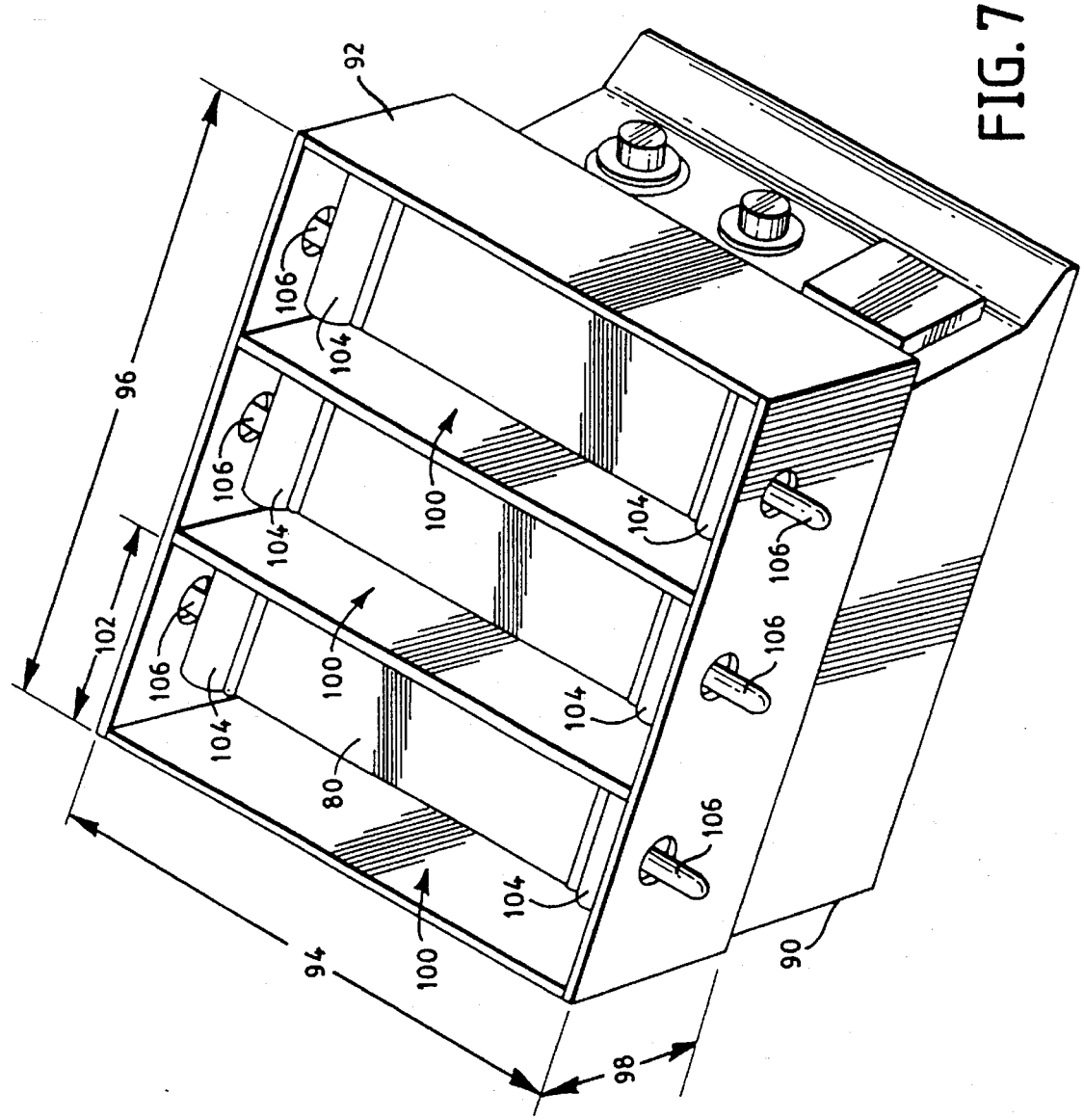
FIG. 7 representatively shows a perspective view of a shake-out testing apparatus.

With reference to FIG. 7, a shaker mechanism 90, such as a Variable Junior Orbit Shaker (Model 3520) available from Lab-Line, is used to determine the ability of the tissue to contain superabsorbent. Alternatively, an equivalent shaker may be employed.

A testing box 92 is operably secured to the shaker, and has four side walls and a cooperating bottom wall, which are constructed of any suitable material, such as clear polycarbonate sheet having a thickness of about 0.025 inch. The box measures approximately 11.5 inch along its length 94, by about 13 inch along its width 96, by 5 inch along its depth 98, and is sectionalized into three compartments 100, each of which is large enough to accommodate the placement of a sample mount therein. Accordingly, each of the shown compartments has inside measurements of approximately 4 inch by 11.5 inch. Each compartment is also equipped with two conventional spring clamps 104 which were positioned on opposed end walls of the compartment and constructed to securely hold the sample mounts in place. One jaw of each spring clamp is securely fastened to its corresponding compartment end wall, and the other jaw is arranged to be free to open and close upon pressure applied to its associated activating lever 106. For testing, the opposite ends of a sample mount were securely held in the pair of clamps attached in the particular compartment employed for testing. The sample mount is positioned with the sample tissue located closest to the bottom wall of the box. The shaker is turned on and operated at an indicated speed of 350 rpm for a period of 5 minutes.

Collection of Superabsorbent

The amount of superabsorbent which is shaken out through the sample tissue is determined by a vacuum collection of the debris. For the following Examples, a 37 mm diameter air monitoring cassette (Gelman Science Product number 4338) is prepared by placing a 37 mm cellulose support pad (Product number 64747) in the bottom of the cassette. A 0.08 micrometer Metricel® membrane (Product number 64678) is placed on top of the support pad, and the top of the cassette is pressed into the mating bottom. The prepared cassette is weighed, and the weight is recorded or tared. The cassette is hooked to a suitable vacuum source with tubing. A plastic funnel is fitted to the tubing, and the superabsorbent is vacuumed into the monitoring cassette. The cassette is reweighed, and the amount of superabsorbent is determined by the weight differential.

EXAMPLES

The following Examples are presented to provide a more detailed understanding of the invention. The Examples are intended to be representative, and are not intended to specifically limit the scope of the invention.

In the present Examples, the indicated abbreviations have the followings meanings:

TAD: Through Air Dried

CWP: Conventional Wet Press

NHWK: Northern Hardwood Kraft fiber

NSWK: Northern Softwood Kraft fiber

SSWK: Southern Softwood Kraft fiber

The indicated vendors have the following locations:

CelluTissue Corporation; 2 Forbes Street; E. Hartford, Conn. 06108

American Tissue Corporation; 1300 Kaster Road; St. Helens, Oreg. 97051

James River Corporation; Natural Dam Division; Gouverneur, N.Y. 13642

The Tables referenced in the Examples, include some shake-out data ("Unavailable Test/Shakeout (rags)") which was generated by an apparatus that had uncertain reliability and is no longer available. The data may be inaccurate or non-representative, but is being made available for the purposes of comparison. In addition, it should be noted that the expression cfm/ft^2" designates the units of, $cfm/ft^2$".

Example A

Example code A was a conventional barrier tissue having a basis weight of about 21.2 gsm and manufactured by a CWP machine process from a furnish composed of 50%/50% Hinton EF (Softwood) and LL-16 (NHWK) fibers. The Hinton EF fiber was obtained from Weldwood, a Division of Canada, Ltd., Hinton, Alberta, Canada; and the LL-16 fiber was obtained from Kimberly-Clark Forest Products, Inc., Terrace Bay, Ontario, Canada. Samples 1–17 were prepared and tested to generate the data summarized in TABLE 1 (FIG. 10).

Example B

Example code B was a conventional forming tissue having a basis weight of about 16.6 gsm and manufactured by a CWP machine process from a furnish composed of 100% LL-19 (NSWK) fiber. The LL-19 fiber was obtained from Kimberly-Clark Forest Products, Inc., Terrace Bay, Ontario, Canada. Samples 1–19 were prepared and tested to generate the data summarized in TABLE 1 (FIG. 10).

Example C

Example code C was a commercial tissue obtained from CelluTissue Corporation. The tissue (Product No. 3030) had a basis weight of about 17.8 gsm and was understood to have been manufactured by a CWP machine process. Samples 1–7 were prepared and tested to generate the data summarized in TABLE 1 (FIG. 10).

Example D

Example code D was a tissue (No. 1-930617-5) having a basis weight of about 17.8 gsm and manufactured by a TAD machine process from a furnish composed of 100% LL-19 (NSWK) refined fiber. Samples 1–27 were prepared and tested to generate the data summarized in TABLE 1 (FIG. 10).

Example E

Example code E was a tissue (No. 2-930615-5) having a basis weight of about 17.6 gsm and manufactured by a CWP machine process from a furnish composed of 100% LL-19 (NSWK), unrefined fiber. Samples 1–26 were prepared and tested to generate the data summarized in TABLE 1 (FIG. 10).

Example F

Example code F was a tissue (No. 2-930615-8) having a basis weight of about 13.2 gsm and manufactured by a CWP machine process from a furnish composed of 100% LL-19 (NSWK) refined fiber. Samples 1–27 were prepared and tested to generate the data summarized in TABLE 1 (FIG. 10A).

Example G

Example code G was a tissue (No. 2-930615-4) having a basis weight of about 15.4 gsm and manufactured by a CWP machine process from a furnish composed of 100% LL-19 (NSWK) unrefined fiber. Samples 1–27 were prepared and tested to generate the data summarized in TABLE 1 (FIG. 10B).

Example H

Example code H was a tissue (No. 1-930616-1) having a basis weight of about 15.4 gsm and manufactured by a TAD machine process from a furnish composed of 50%/50% CR-55 (SSWK) fiber and LL-19 (NSWK) refined fiber. The CR-55 fiber was obtained from Kimberly-Clark Corporation, Coosa Pines, Ala. Samples 1–28 were prepared and tested to generate the data summarized in TABLE 1 (FIG. 10B).

Example I

Example code I was a tissue (No. X3P-295) having a basis weight of about 16.1 gsm and manufactured by a CWP machine process from a furnish composed of 50%/50% Eucalyptus (Hardwood) fiber and LL-19 (NSWK) refined fiber. Samples 1–6 were prepared and tested to generate the data summarized in TABLE 1 (FIG. 10B).

Example J

Example code J was a commercial tissue obtained from James River Corporation (Product No. 35484) and is understood to have been manufactured by a CWP machine process. Samples 1–6 were prepared and tested to generate the data summarized in TABLE 1 (FIG. 10A).

Example K

Example code K was a commercial tissue obtained from American Tissue Corporation (Product Code 9321-66-195, 1-ply porous carrier) having a basis weight of about 17.1 gsm and is understood to have been manufactured by a CWP machine process. Samples 1–9 were prepared and tested to generate the data summarized in TABLE 1 (FIG. 10B).

Example L

Example code L was a commercial tissue obtained from American Tissue Corporation (Product Code 9321-88-195, 1-ply carrier, non-porous) having a basis weight of about 16.4 gsm and is understood to have been manufactured by a CWP machine process. Samples 1–9 were prepared and tested to generate the data summarized in TABLE 1 (FIG. 10B).

Examples D, E, F, G and I are representative of face sheets suitable for the present invention.

Figure 11:
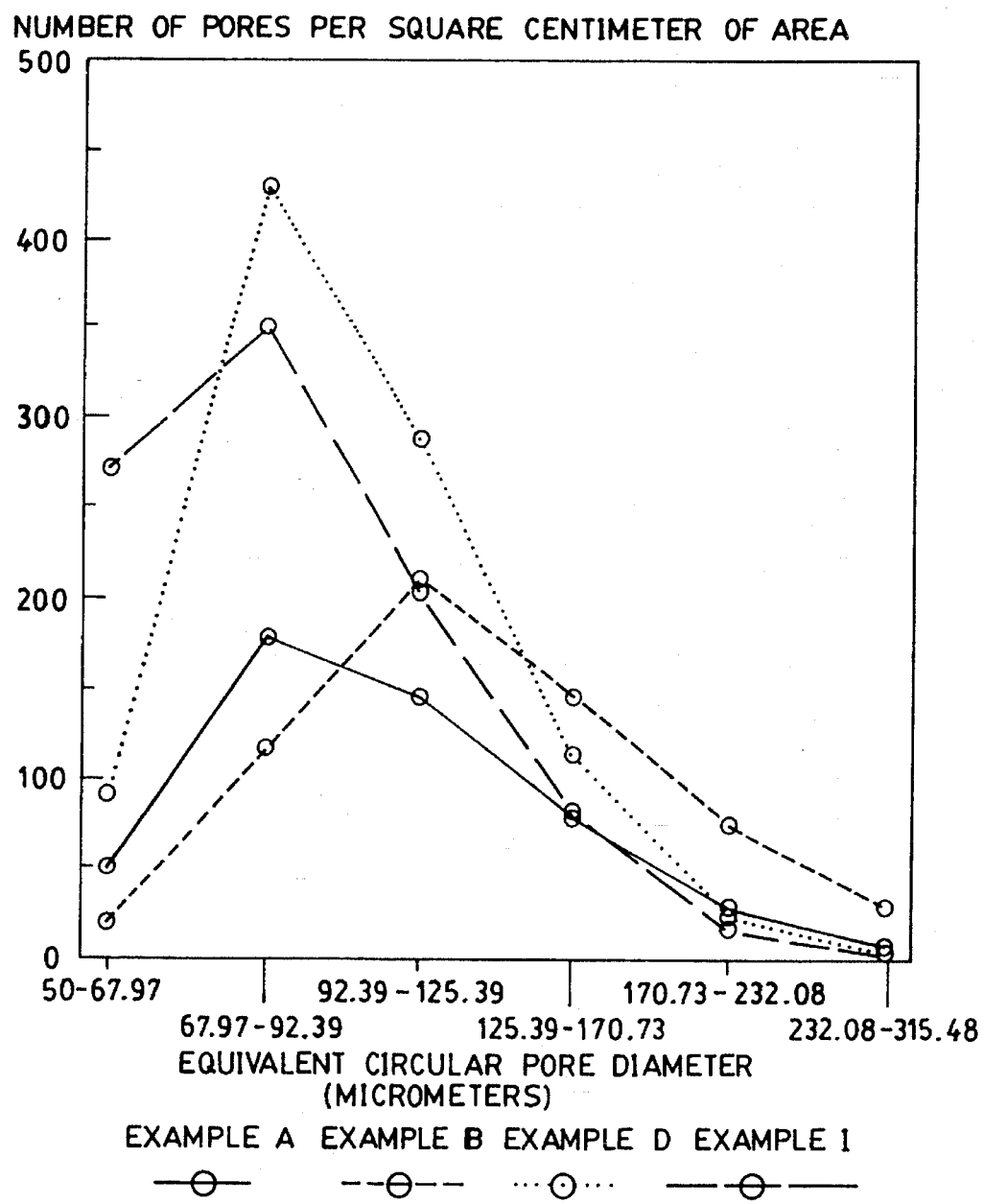
FIG. 11 shows a graph of Pore Count vs. Pore Size which shows a representative comparison between the face sheet layers of Examples A, B, D and I.

With reference to FIG. 11, the graph for Example A representatively shows that the material has a relatively small total number of pores, and as a result, exhibits low air permeability. The graph for Example B representatively shows that the material has a large number of large diameter (ECD) pores, and as a result, exhibits high air permeability but can allow an escape of an excessive amount of particles through the large pores. The graphs for Examples D and I representatively show that the materials each have a relatively large number of small pores combined with a relatively small number of large pores, and as a result, can exhibit an advantageous combination of high air-permeability and improved containment of superabsorbent particles.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:

a backsheet layer, an absorbent structure superposed on said backsheet layer, said absorbent structure including particles of high absorbency material;

a liquid permeable topsheet layer superposed on said absorbent structure to sandwich said absorbent structure between said topsheet layer and said backsheet layer; and a fibrous face sheet layer connected to said article for restraining a movement of said high absorbency material from selected regions of said absorbent structure, said face sheet layer having a Frazier Porosity value of at least about 150 cubic feet per minute per square foot of surface area, having not more than about 100 pores, per 31.37 cm$^2$ of surface area, with a pore size greater than about 300 micrometers, and having at least about 9,500 pores, per 31.37 cm$^2$ of surface area, with pore sizes within a range of about 67.97–92.39 micrometers.

2. An absorbent article as recited in claim 1, wherein said face sheet layer has at least about 11,000 pores, per 31.37 cm$^2$ of surface area, with pore sizes within a range of about 67.97–92.39 micrometers.

3. An absorbent article as recited in claim 1, wherein said face sheet layer has not more than about 350 pores, per 31.37 cm$^2$ of surface area, with pore sizes within a range of about 232.08–315.48 micrometers.

4. An absorbent article as recited in claim 2, wherein said face sheet layer has not more than about 350 pores, per 31.37 cm$^2$ of surface area, with pore sizes within a range of about 232.08–315.48 micrometers.

5. An absorbent article as recited in claim 1, wherein said face sheet layer has not more than about 300 pores, per 31.37 cm$^2$ of surface area, with pore sizes within a range of about 232.08–315.48 micrometers.

6. An absorbent article as recited in claim 4, wherein said face sheet layer has not more than about 300 pores, per 31.37 cm$^2$ of surface area, with pore sizes within a range of about 232.08–315.48 micrometers.

7. An absorbent article as recited in claim 1, wherein said face sheet layer has a Frazier Porosity value of at least about 175 cfm/ft$^2$.

8. An absorbent article as recited in claim 1, wherein said face sheet layer has a Frazier Porosity value of at least about 200 cfm/ft$^2$.

9. An absorbent article as recited in claim 1, wherein face sheet layer has a basis weight of at least about 8 gsm.

10. An absorbent article as recited in claim 1, wherein face sheet layer has a basis weight of not more than about 40 gsm.

11. An absorbent article as recited in claim 1, wherein absorbent structure includes a fibrous matrix which contains high absorbency particles therein and is located adjacent said face sheet layer.

12. An absorbent article as recited in claim 1, wherein absorbent structure includes an high absorbency laminate having high absorbency material located in a selected array of pocket regions located on said face sheet layer.

13. An absorbent article as recited in claim 12, wherein absorbent structure includes a distribution layer positioned generally adjacent an outer side surface of said absorbent laminate.

14. An absorbent article as recited in claim 13, wherein absorbent structure includes a first face sheet located adjacent a bodyside surface of said absorbent laminate and a second face sheet layer located adjacent a bodyside surface of said distribution layer.

15. An absorbent article, comprising:

a backsheet layer;

an absorbent structure superposed on said backsheet layer, said absorbent structure including particles of high absorbency material;

a liquid permeable topsheet layer superposed on said absorbent structure to sandwich said absorbent structure between said topsheet layer and said backsheet layer; and a fibrous face sheet layer connected to said article for restraining a movement of said high absorbency material from selected regions of said absorbent structure, said face sheet layer having a Frazier Porosity value of at least about 150 cubic feet per minute per square foot of surface area, having not more than about 100 pores, per 31.37 cm$^2$ of surface area, with a pore size greater than about 300 micrometers, having at least about 9,500 pores, per 31.37 cm$^2$ of surface area, with pore sizes within a range of about 67.97–92.39 micrometers, and having a particle Shake-out value of not more than about 60 mg.

16. An absorbent article as recited in claim 15, wherein at least a proportion of said high absorbency particles have a particle size of less than about 300 micrometers.

17. An absorbent article as recited in claim 15, wherein said face sheet layer has a Frazier Porosity value of at least about 175 cfm/ft$^2$.

18. An absorbent article as recited in claim 15, wherein said face sheet layer has a Frazier Porosity value of at least about 200 cfm/ft$^2$.

19. An absorbent article as recited in claim 16, wherein said face sheet layer has a particle Shake-out value of not more than about 40 mg.

20. An absorbent article as recited in claim 16, wherein said face sheet layer has a particle Shake-out value of not more than about 20 mg.

* * * * *